US012609205B2

(12) United States Patent
King

(10) Patent No.: US 12,609,205 B2
(45) Date of Patent: Apr. 21, 2026

(54) ECOSYSTEM FOR LONG TERM CARE FACILITY

(71) Applicant: BioLink Systems LLC, Cincinnati, OH (US)

(72) Inventor: Roger King, Hamilton, OH (US)

(73) Assignee: BioLink Systems LLC, Cincinnati, OH (US)

( * ) Notice: Subject to any disclaimer, the term of this patent is extended or adjusted under 35 U.S.C. 154(b) by 0 days.

(21) Appl. No.: 18/929,988

(22) Filed: Oct. 29, 2024

(65) Prior Publication Data

US 2026/0088180 A1 Mar. 26, 2026

Related U.S. Application Data

(60) Provisional application No. 63/699,136, filed on Sep. 25, 2024.

(51) Int. Cl.
G16H 50/30 (2018.01)
G16H 40/67 (2018.01)

(52) U.S. Cl.
CPC ............. G16H 50/30 (2018.01); G16H 40/67 (2018.01)

(58) Field of Classification Search
CPC ............................... G16H 50/30; G16H 40/67
See application file for complete search history.

(56) References Cited

U.S. PATENT DOCUMENTS 10,322,036 B2    6/2019  King et al.
10,561,541 B1    2/2020  King et al.

10,713,372 B1     7/2020   King et al.
10,786,210 B1     9/2020   King et al.
10,821,034 B2    11/2020   King et al.
10,940,484 B2     3/2021   King et al.
11,020,285 B1     6/2021   King et al.
11,123,232 B2     9/2021   King et al.
11,166,858 B1    11/2021   King et al.
11,207,219 B1    12/2021   King et al.
11,638,564 B2     5/2023   King et al.
12,396,688 B2     8/2025   King et al.
2011/0234395 A1*  9/2011   Johnson et al.
2015/0106123 A1*  4/2015   Amarasingham et al.
2015/0125832 A1*  5/2015   Tran
2018/0117298 A1*  5/2018   Tessarin (Continued)

FOREIGN PATENT DOCUMENTS

CN          213218078        *   5/2021

*Primary Examiner* — Michael I Ezewoko
*Assistant Examiner* — William T. Monticello
(74) *Attorney, Agent, or Firm* — Chris Tanner; FYPA PLLC

(57)                    ABSTRACT

An ecosystem and platform for use within Long Term Care Facilities (LTCFs) enhances flow of accurate, usable medical data, and improves work atmosphere within typical nursing homes. These features include but are not limited to changes to call lights, changes to management of bed elevation, changes to data management, and changes to how nursing home workers and staff are compensated and incentivized. This ecosystem and platform leverages technology advances to be more effective in a nursing home environment. These features are all tied together to communicate directly to the staff via a single handheld device with data flowing through a centralized information hub that identifies patient needs.

15 Claims, 14 Drawing Sheets

(56) References Cited

U.S. PATENT DOCUMENTS

| | | | |
|---|---|---|---|
| 2018/0247713 A1* | 8/2018 | Rothman | |
| 2018/0279880 A1* | 10/2018 | Bacchi | |
| 2020/0364182 A1* | 11/2020 | Threlkeld | |
| 2021/0319894 A1* | 10/2021 | Sobol | |
| 2023/0010793 A1* | 1/2023 | Testani et al. | |
| 2023/0013233 A1* | 1/2023 | Kayser et al. | |
| 2023/0210372 A1* | 7/2023 | Alam et al. | |

* cited by examiner circuit board 137 mechanical clip 139 wireless means 138 existing
call light call light module 136

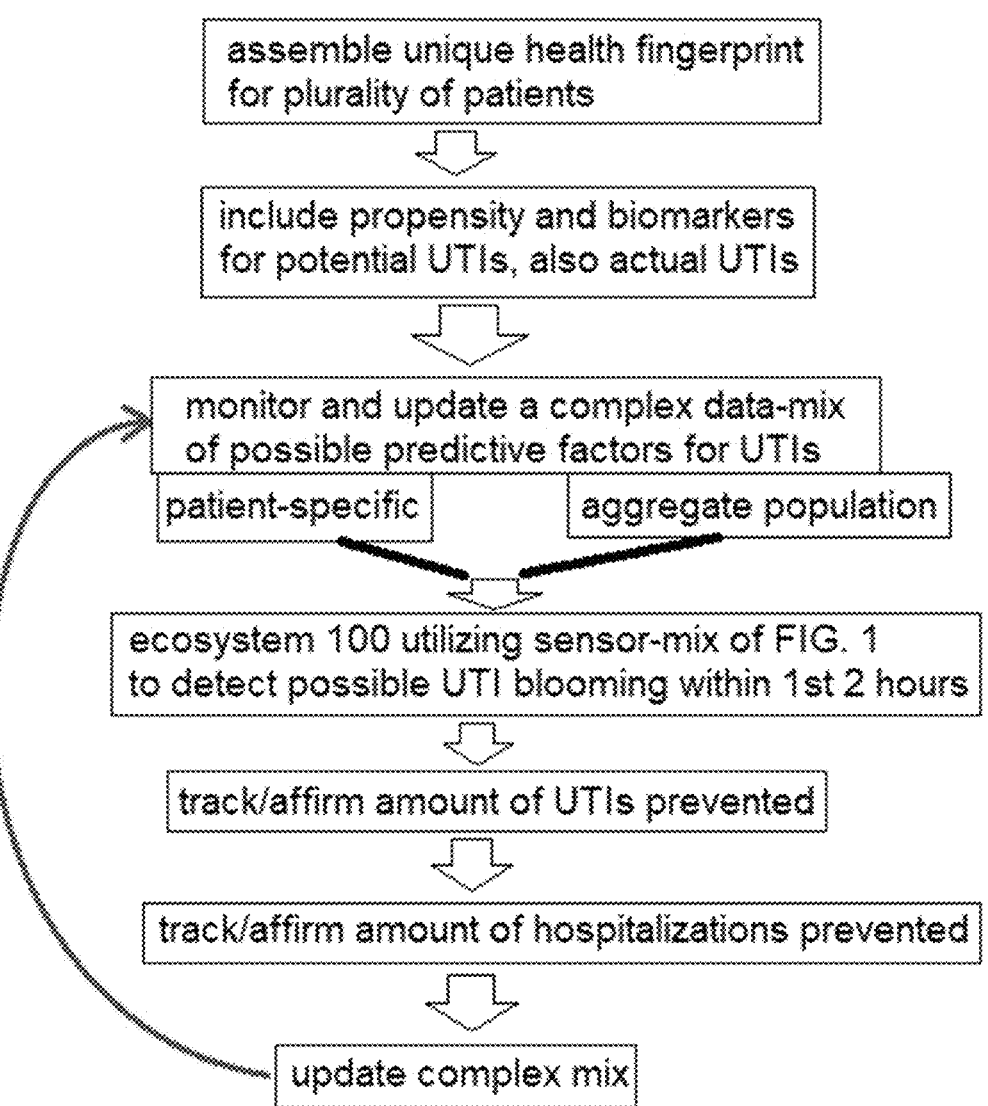

Process for early intervention
<UTI example> assemble unique health fingerprint
for plurality of patients include propensity and biomarkers
for potential UTIs, also actual UTIs monitor and update a complex data-mix
of possible predictive factors for UTIs patient-specific    aggregate population ecosystem 100 utilizing sensor-mix of FIG. 1
to detect possible UTI blooming within 1st 2 hours track/affirm amount of UTIs prevented track/affirm amount of hospitalizations prevented update complex mix

FIG. 7A

Process for early intervention
<feeding tube example> assemble unique health fingerprint
for plurality of patients

factor in the various reasons they are on
feeding tubes now, and type of tube

monitor and update a complex data-mix
of possible predictive factors for F-tube problems

| patient-specific | aggregate population |

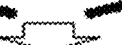

ecosystem 100 utilizing sensor-mix of FIG. 1
to detect possible F-tube issues within
<predetermined time period>

track/affirm amount of F-tube problems prevented

track/affirm amount of hospitalizations prevented

update complex mix

FIG. 7B

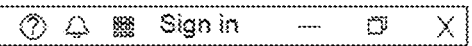
CLINICAL OUTCOME REPORT
Pulse, PulsOx, Body-Temp
Time-Span: Jun 1 20XX to November 30 20XX
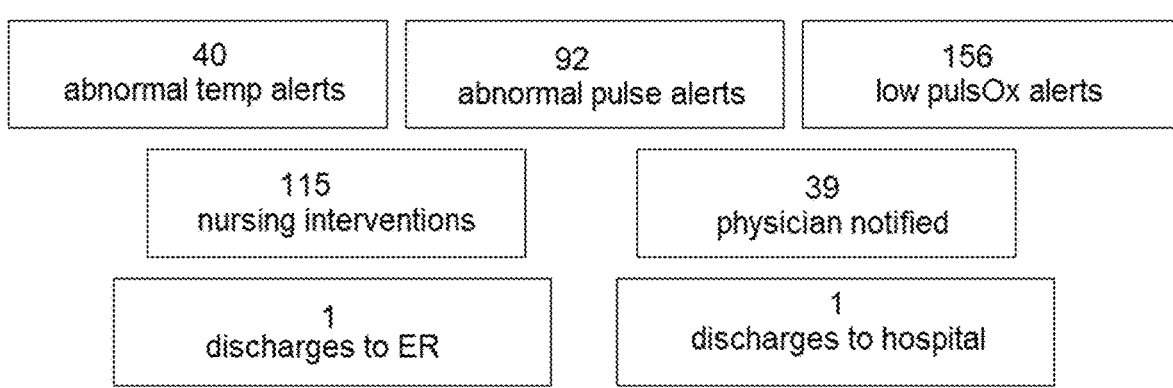
2,184
patient days
| 40 abnormal temp alerts | 92 abnormal pulse alerts | 156 low pulsOx alerts |
115
nursing interventions
39
physician notified
1
discharges to ER
1
discharges to hospital
FIG. 8

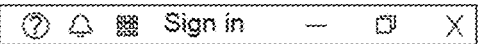
CLINICAL OUTCOME REPORT
incontinence care, skin health, and UTI
time-span: Jun 1 20XX to November 30 20XX
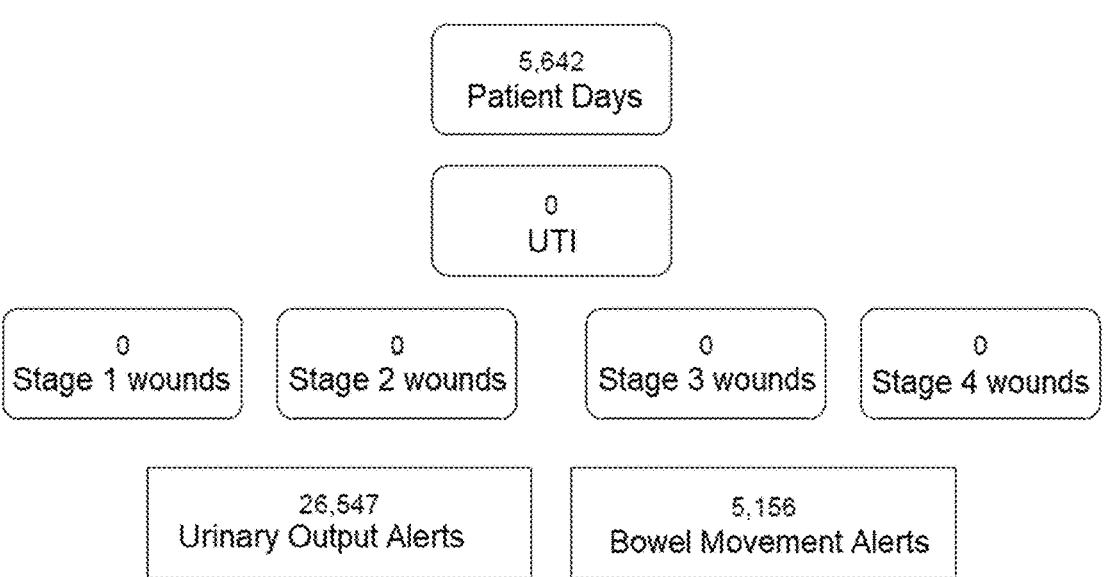
| 5,642 |
| Patient Days |
| 0 |
| UTI |
| 0 | 0 | 0 | 0 |
| Stage 1 wounds | Stage 2 wounds | Stage 3 wounds | Stage 4 wounds |
| 26,547 | 5,156 |
| Urinary Output Alerts | Bowel Movement Alerts |
AVERAGE RESPONSE TIMES (hrs)
| without ecosystem 100 | using ecosystem 100 | using ecosystem 100 plus rewards program (FIG. 12) |
|---|---|---|
| 6.25 Hours | 1.44 Hours | 0.90 Hours |
FIG. 9

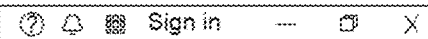

CLINICAL OUTCOME REPORT

Decreased Urinary Output and Fecal Impaction

Time-Span: Jun 1 20XX to November 30 20XX 5,642
Patient Days

108
Decrease Urinary Output Alerts

54
Possible Fecal Impaction Alerts

100%
Accuracy Triggering Nursing Bedside Assessments

90%
Alerts Resulted in Nursing Interventions or
Physician Orders

0
Alerts Resulted in Discharges to ER

0
Alerts Resulted in Discharges to
Hospital

FIG. 10

RETENTION REPORT FOR LABOR-CLASS:  CNA

Time-Span:  Jun 1 20XX to November 30 20XX

| CNA Staff | | CNA Staff who Quit |
|---|---|---|

| 4 Week Av. Incentives Earned $100 | 4 Week Earning Range $26-$344 | Total Incentive Paid $14857 |
|---|---|---|

| National Turnover Rate 53.9% | Kansas Turnover Rate 58.1% | Turnover Rate at locations using ecosystem 100 2% |
|---|---|---|

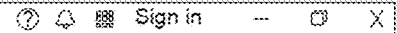

RETENTION REPORT FOR LABOR-CLASS:  CNA

Time-Span:  Jun 1 20XX to November 30 20XX

| CNA Staff | CNA Staff who Quit |
|---|---|

| 4 Week Av. Incentives Earned<br>$100 | 4 Week Earning Range<br>$26-$344 | Total Incentive Paid<br>$14857 |
|---|---|---|

| National Turnover Rate<br>53.9% | Kansas Turnover Rate<br>58.1% | Turnover Rate at locations<br>using ecosystem 100<br>2% |
|---|---|---|

| <using ecosystem 100><br>hospital admissions <u>prevented</u>: 113 | typical KS hospital admissions prevented:  unknown<br><most LTCFs have no way to measure this> |
|---|---|

FIG. 11B

REWARD POINTS REPORT

| Alert Type | Moisture Type | Responder | Time To Resolve | Sum of Dollars Earned | Points Earned | Resolved At |
|---|---|---|---|---|---|---|
| moisture | Urine | Bobby | 1.82 | $2.00 | 4 | 10/3/2023 7:36:22 PM |
| moisture | Urine | Joey | 4.16 | $0.00 | 0 | 10/3/2023 7:38:54 PM |
| moisture | Urine | Annete | 1.24 | $2.00 | 4 | 10/3/2023 7:50:59 PM |
| moisture | Urine | Jean | 1.92 | $2.00 | 4 | 10/3/2023 9:56:22 PM |
| moisture | BM | Pam | 0.93 | $2.50 | 5 | 10/4/2023 12:45:35 PM |
| moisture | Urine | Ralph | 1.28 | $2.00 | 4 | 10/4/2023 7:15:10 PM |
| moisture | BM | Lynda | 1.56 | $2.00 | 4 | 10/4/2023 8:20:27 PM |
| moisture | Urine | Carter | 2.25 | $1.50 | 3 | 10/4/2023 8:23:19 PM |

ECOSYSTEM FOR LONG TERM CARE FACILITY

BACKGROUND OF THE INVENTION

Long Term Care Facilities (LTCFs) are under extreme pressure to reduce costs. At the same time, the liability for error has never been higher, even innocent error. Consequently, a mechanism for improved management of LTCFs is desired.

SUMMARY OF THE INVENTION

The embodiments herein disclose a number of features which make a nursing home or assisted living facility into a type of ecosystem which enhances flow of accurate, usable medical data, and also is a much better place to work than typical nursing homes. These features include but are not limited to changes to call lights, changes to management of bed elevation, changes to data management, and changes to how nursing home workers and staff are compensated and incentivized. This ecosystem leverages technology advances to be more effective in a nursing home environment. These advances are all tied together conceptually to communicate directly to the staff via a single handheld device with data flowing through a centralized information hub that identifies patient needs.

Minor health issues can progress toward crisis-levels very quickly with elderly patients, which can have negative outcomes. To address this, the various embodiments of ecosystem(s) described herein facilitate timely/quick interventions and greatly reduce negative outcomes. The platform nature of the embodiments herein accommodates current technology, can be adapted toward future technology, and also provides an opportunity platform for $3^{rd}$ party technology developers. Specifically, the embodiments herein leverage changes in technology to create a growing changing platform that third party developers can use as a base, in order to produce their own customized improvements. A configurable platform allows for plugging in of various 3d party devices that may exist now or may be built in the future, helpful in monitoring for different risk factors. When any of these various health events occur, the nursing home staff is notified in a variety of convenient ways.

One main goal of the embodiments herein is to identify risks based on the plethora of data points being gathered and assessed. This should include all the data points of a particular patient.

SUMMARY/SEMANTICS

Within this disclosure, the terms used will strive to be agnostic to age, and mainly refer to a long-term care facility (LTCF) or perhaps a skilled nursing facility (SNF). The patients could be seniors, but could also be 20 year olds. Within this disclosure, it is important to bear in mind that a 20 year old can have a stroke and need a LTCF, although this is rare. This disclosure will largely refer to LTCF and avoid terms such as "senior care" or "nursing home" as that is an over-simplification and may connote something that is misleading.

Another important factor about the embodiments herein is the focus not just on identifying various risk factors, as much Prior Art does that. Instead, the embodiments herein focus on properly interpreting those risk factors and then triggering an intervention, but an effective, informed intervention that is timely. That is really difficult because even with all these medical devices attached, there are all kinds of false alarms and misreadings that must be filtered out.

IOW, there will be plenty of Prior Art that identifies risk factors, but contains only minimal discussion of types of interventions, and their effectiveness. Such resources provide only minimal benefit. IOW, various Prior Art implementations often only identify risk, and not always reliably, but do not trigger effective interventions.

Next, some clarification on the word "aggregate" as used herein. An environment where the key demographic is elderly, but not exclusively elderly may sometimes be labeled as "aggregate living". It is important to remember that aggregate living is different than skilled nursing facility (SNF). Aggregate living is where everything is achieved environmentally e.g. from intervention to food to pharmacy to activity, to physical therapy, to social/recreation items, this is all "aggregated" under one roof.

Meanwhile, the embodiments herein use the word "aggregate" in a very different context, instead referring to long term care facilities (LTCF) or skilled nursing facilities (SNF). An LTCF or SNF can operate for hundreds of people, not just one person thus being aggregated, meaning they aggregate human patients, but do not aggregate features. The embodiments herein may work on hundreds and perhaps thousands under one roof, so that is what is meant (herein) by the word "aggregated". But also, the embodiments herein are targeted toward situations where everyone has impairment, either elderly or non-elderly but disabled Meanwhile, it is also true that some SNFs have smaller numbers of people in them, for example as few as 3 people. The embodiments herein apply to such SNFs including 3-patient SNFs as well.

Next, this disclosure will discuss items such as smart brief, garments, wearables including but not limited to watches, glasses, and other smart clothing. These items all provide types of biomarkers.

The embodiments herein comprise a way of leveraging sensors that provide useful biomarker information. However, examples of existing sensors are just that, mere examples for the purpose of explanation \enablement, and the embodiments herein should not be considered as limited thereto. Some biomarker-sensors may exist at this time, but the platform nature of the embodiments is intended to accommodate all kinds of bio-innovations, including those that are coming soon or may only exist in the future.

Along these lines, this disclosure will refer to a "health fingerprint", and some example components of a health fingerprint will be suggested herein. However, this should not be considered limiting, and again in keeping with the embodiments herein being a "platform" and not just a static fixed un-changing resource, the use of health fingerprint and other expressions should be read to include potential future biosensors and biomarkers.

A final semantic point: the word "alert" is often used within this disclosure, including sometimes as a noun, and sometimes as a verb. Should there be any ambiguity, the author will try to make it clear which usage is meant.

BRIEF DESCRIPTION OF DRAWINGS

FIGS. 7A (UTI) and 7B (feeding tube) show non-limiting example flowcharts of successful operation;

FIG. 8 shows an example non-limiting GUI derived from either the wrist wearable device or some other device which effectively measures patient body temperature;

FIG. 9 shows a GUI displaying various improvements in incontinence care and skin health;

FIG. 10 shows alerts managed by the ecosystem\platform suitable for monitoring individual resident incontinent episodes for bowel and bladder;

FIG. 11B shows a type of evidence-based computation; and

DETAILED DESCRIPTION OF THE PREFERRED EMBODIMENTS

Figure 1:
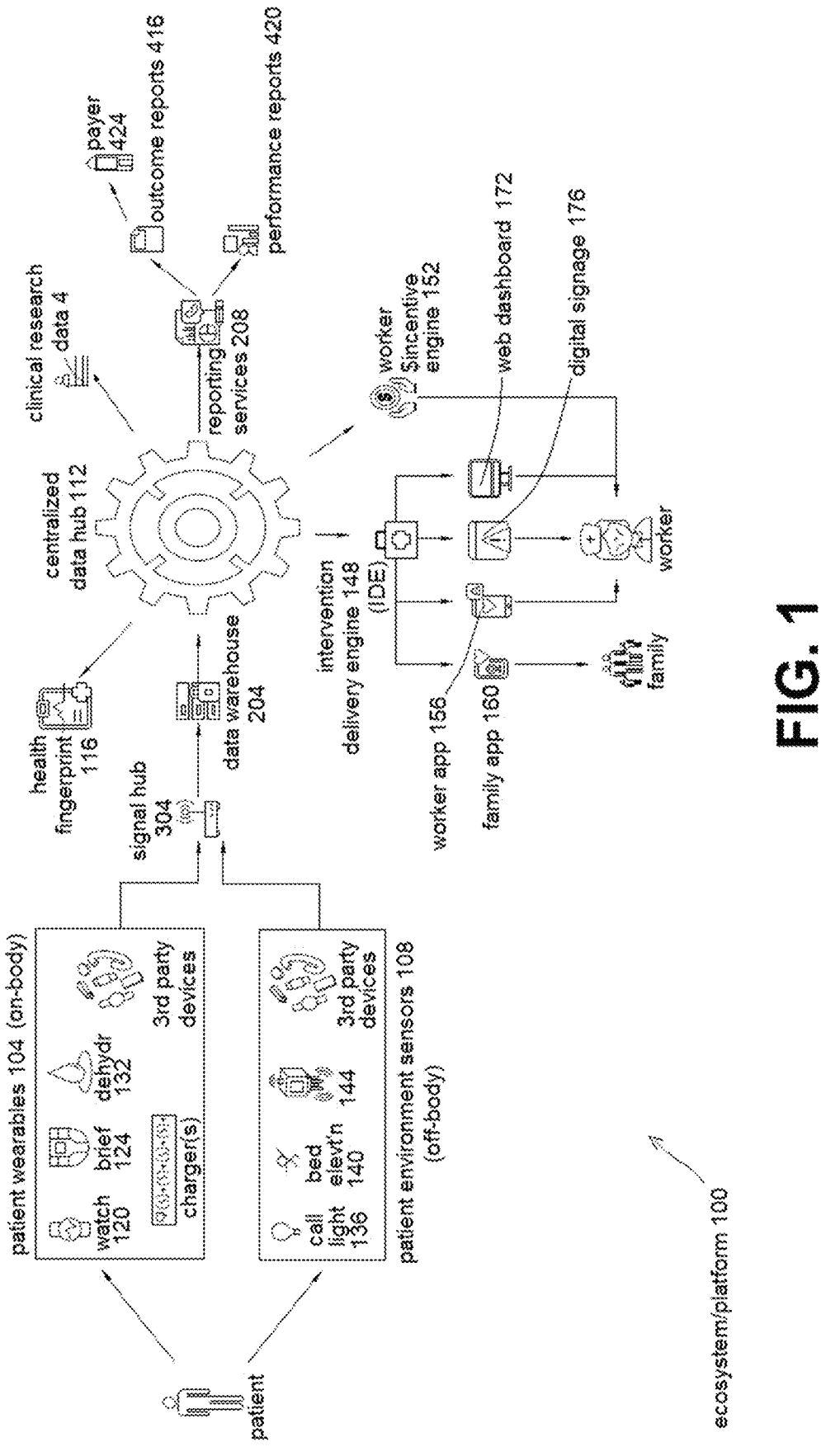
FIG. 1 shows an example ecosystem.

An example ecosystem 100 is shown in FIG. 1, with some core components overtly labeled, while other components are shown but labeled elsewhere with respect to later Figures herein. This is for the purpose of simplicity and readability, and preventing any single Figure from becoming overly busy or overly cluttered.

Like any good long term care facility (LTCF), FIG. 1 starts with the patient(s), who are monitored by a variety of on-body (104) and off-body (108) patient data-sensing resources. The on-body wearables 104 include but are not limited to a watch (wrist-wearable) 120, a brief (garment) 124, and a dehydration sensor 132, as well as any of numerous 3$^{rd}$ party devices for monitoring patient data. All of these devices may have a variety of wireless communication protocols, chargers, and various ways of managing inventory and performing repairs.

The various off-body (environment) devices 108 will include but are not limited to the call light monitor 136, the bed elevation monitor 140; the humidity\temperature\ambientNoise monitor 144; air quality monitor; light intensity monitor, and any of numerous 3$^{rd}$ party devices for monitoring patient environment data.

These devices 104/108 work together to create a health fingerprint 116 that is unique to each patient, which works with a centralized data hub 112 to continuously refine and maintain accuracy of that health fingerprint 116.

As suggested within FIG. 1, bio-data measurements will be gathered from on-body wearable devices 104 as well environment-based (off-body) devices 108. Additional on-body mechanisms 104 can include but not limited smart glasses; smart clothing; smart wound patches/bandages (with RF capability); smart neck and ankle bracelets; smart medication dispensers; and/or other biomarker sensors not explicitly shown herein, including being provided by 3$^{rd}$ parties. Thus, FIG. 1 is for example-only, so that the embodiments herein should not be considered as limited exclusively thereto.

The on-body devices 104 will monitor vital signs comprising urination; BM; skin temperature; body temperature; glucose level; heart rate; pulseOx; ECG; hydration; blood pressure; cognitive function; mood; UV exposure; wound healing state; and future biomarkers not necessarily shown in FIG. 1.

As shown with respect to FIG. 1, the wearable (on-body) devices 104 include but are not limited to the diaper brief 124. Watches, glasses, clothing, wound patches, bandages, neck, ankle bracelets, and medical dispensers are all contemplated within the embodiments herein. The wound patch may have a small Bluetooth transmitter, or NFC, or other low power or passive wireless communication mechanism.

The centralized data hub 112 works with a signal hub 304 (FIG. 3) to manage and coordinate the plethora of data signals originating from the diverse array of on-body 104 and off-body 108 data sensors. These all may have differing signal-protocols, packets, and other unique communication parameters. Fortunately, the signal hub 304 manages all the diverse communications but does not digest data or make decisions. It sends data to the data hub which makes decisions and talks to the intervention delivery engine 148. This in turn means that a nursing home worker only needs one single device, a single mobile device bearing the worker app 156.

The centralized data hub 112 assists with data processing and decisions made by the ecosystem 100. It is helpful that the ecosystem/platform 100 is flexible and accommodates a wide variety of medical devices. This way, the on-body 104 and off-body 108 devices can take many forms, have all kinds of different features, chargers, signals, protocols, and yet the worker only needs to carry one single mobile device bearing the worker app 156.

As a result of this, the interventions sent to the worker are targeted, accurate, and false alarms are minimized. This is because the centralized data hub 112 and intervention delivery engine 148 screen, filter, assign priority, and sort among the high volume of medical data to give a high degree of assurance that the worker receives exactly the data she needs to do an effective, targeted patient intervention, and yet receive only that data and no more.

An important term herein will be the "health fingerprint" 116 shown at least within FIG. 1. Specifically, the health fingerprint 116 comprising an individual patient's health state will be built, continuously maintained, and adjusted by the ecosystem 100. This health fingerprint 116 will be an aggregate of vital sign measurements collected from each patient. This aggregate will establish a baseline and deviations from this baseline will be detected and help identify of possible risk factors which vary from patient to patient.

Detected anomalies and risk factors will allow for early detection of health changes associated with the following conditions comprising hypertension; heart disease; heart failure; pneumonia; UTI; diabetes; kidney failure; hearing loss; depression; cognitive decline; long healing wounds; Skin breakdowns; mood changes; fecal impaction; dehydration; infections, and other changes in health conditions associated with any current and future biomarker sensors.

FIG. 1 also shows a worker app 156, a family app 160, a web dashboard 172, and digital signage 176. The web dashboard 172 can give an executive view of one or more LTCFs using the ecosystem 100. The worker app 156 is installed on a mobile device each unique to a specific worker, and is the only communication mechanism they need to be effective. The family app 160 can be helpful when a patient is located in a family home.

Figure 2:
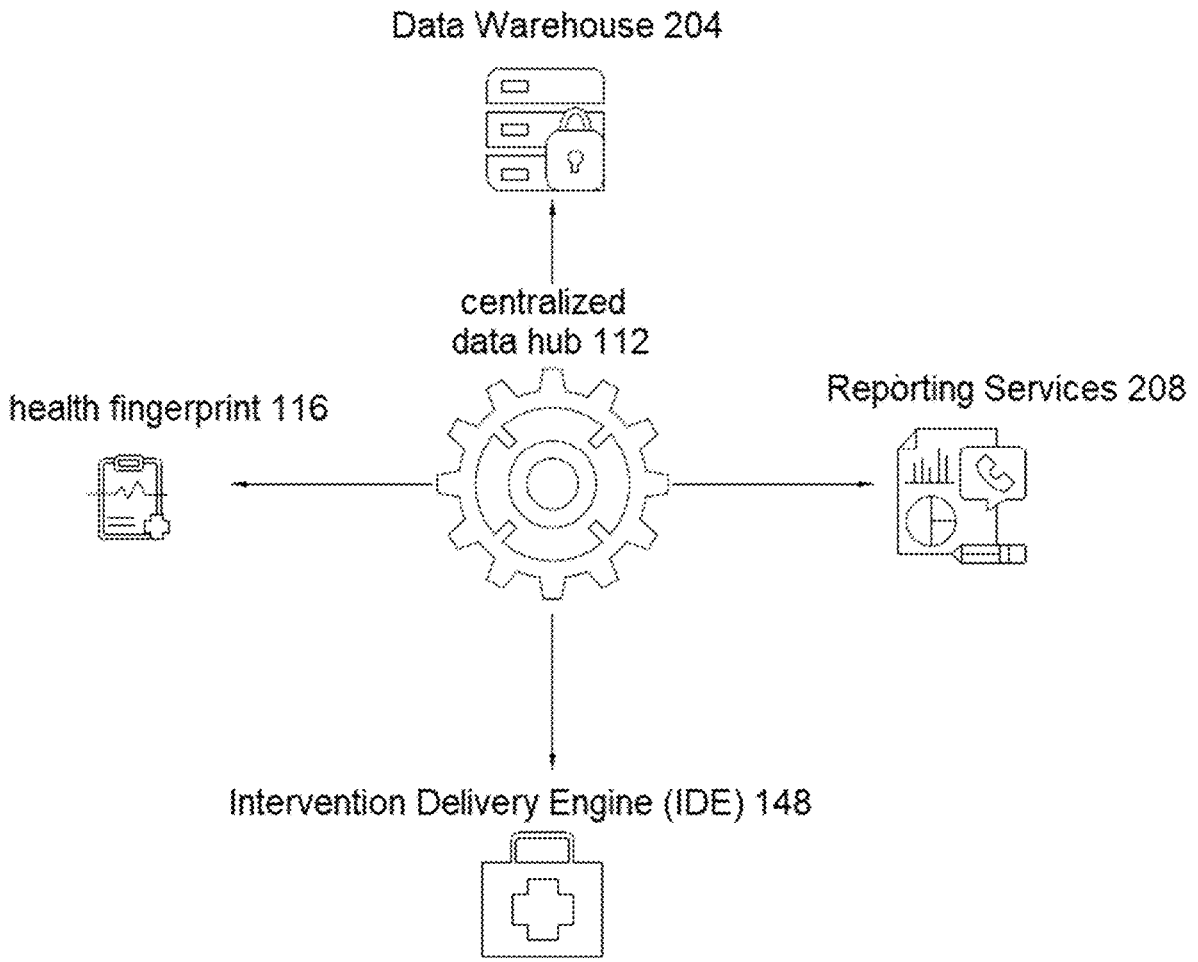
FIG. 2 provides clarification to FIG. 1 including a data warehouse and a group of reporting services.

FIG. 2 provides some clarification to some elements within FIG. 1 including a data warehouse 204 and a group of reporting services 208. The data warehouse 204 is capable of storing hundreds of millions of data points. That is helpful because the ecosystem/platform 100 manages a high volume of data over a broad (aggregate) spectrum of human patients. This results in a ton of data, which is continually updated. It would not be possible to create an effective health fingerprint 116 without a strong robust resource such as the data warehouse 204.

Next, the various reporting services 208 are key because currently, LTCFs have no way to have a real time view of what's happening in any particular facility. The reporting services 208 allow facility management to use the ecosystem/platform 100 to monitor performance and make needed adjustments in near real time.

Figure 3:
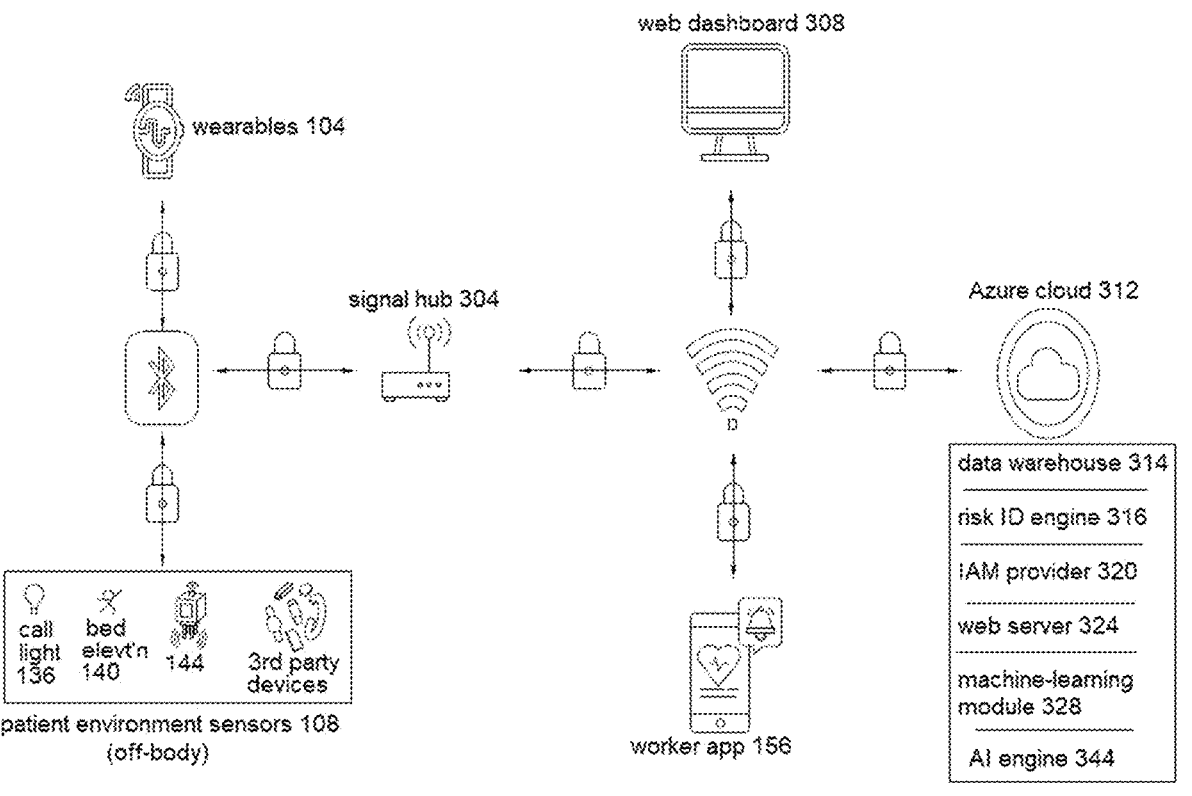
FIG. 3 shows a signal hub and web dashboard.

FIG. 3 provides some depth and context to FIG. 1, showing a signal hub 304 and web dashboard 308 that were suggested but somewhat buried within FIG. 1. FIG. 3 is an expanded view of various elements within the ecosystem/platform 100. FIG. 3 shows some aspects of signal-routing and flow-directionality that would not have fit within FIG. 1, as FIG. 1 is a very congested figure.

FIG. 3 also shows more detail about the cloud 312, including the data warehouse 314, risk ID engine 316, IAM provider 320, web server 324, machine-learning module 328, and AI engine 344. The signal hub 304 routes various types of data to the cloud storage 312, which in an embodiment can be Azure. However, other types of non-Azure cloud mechanisms are also contemplated herein.

Figure 4:
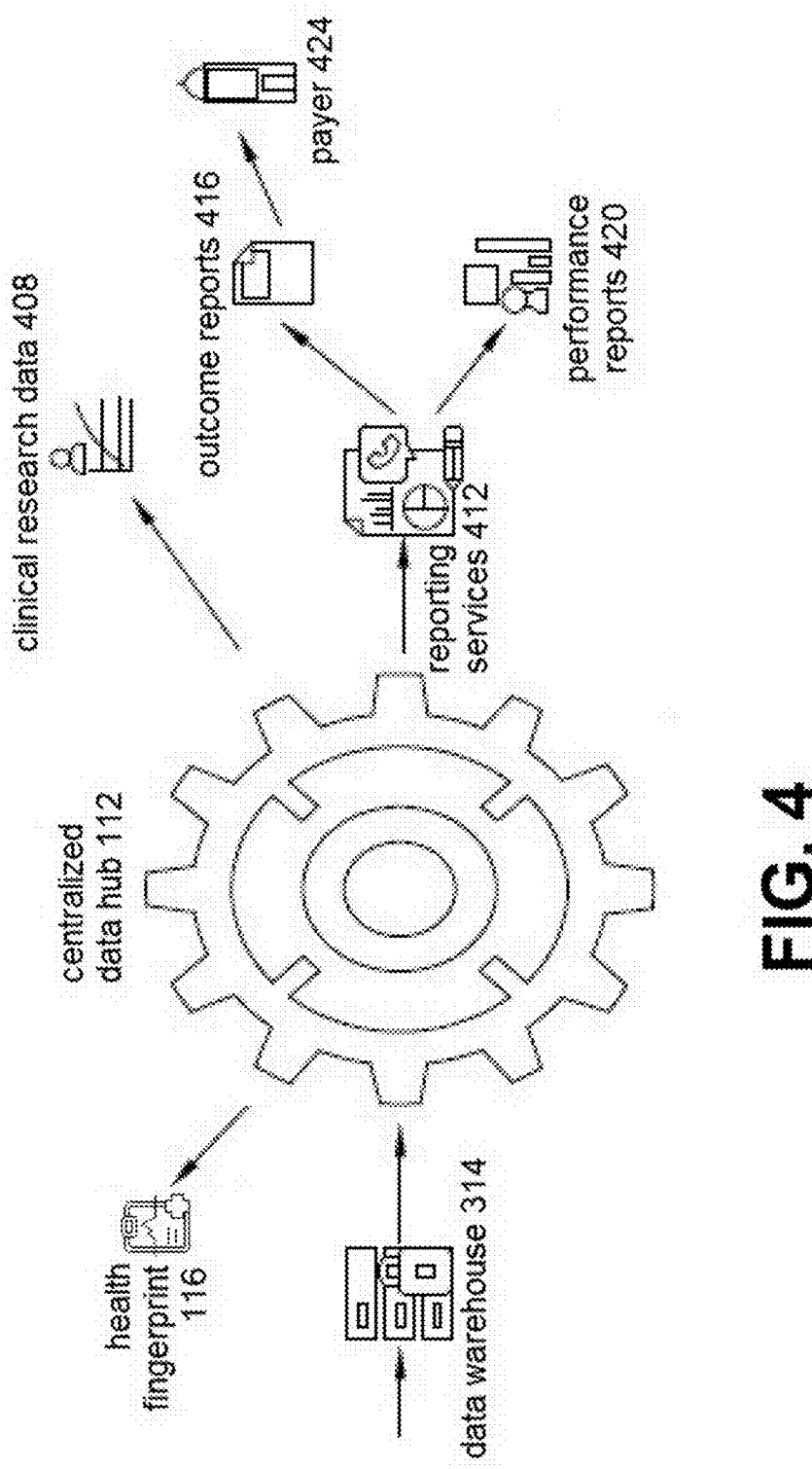
FIG. 4 shows a clinical research data module, reporting services, outcome reports, performance reports, and a payer.

FIG. 4 also shows other elements that may be in FIG. 1 but are re-recited in more detail in FIG. 4, comprising a clinical research data module 408, reporting services 208, outcome reports 416, performance reports 420, and a payer 424.

The clinical research data module 408 (hereinafter, module 408) is involved in collecting clinical data including allowing 3rd parties to use data for research, and also allowing 3rd parties to put a device into the ecosystem 100 to collect clinical data for research.

The outcome reports 416 reports showing what impact the ecosystem\platform 100 had on patients. This includes but is not limited to reductions of UTIs, reductions in skin breakdowns, & many other gains.

The payer 424 has a strong incentive to see reductions of unfavorable health conditions since they are paying for it. They want to see reports formatted in a specific way that is helpful for financial analysis.

Consider an example where a patient gets a UTI, and has to be removed to a hospital at considerable expense. The payer 424 would be the entity that ends up eating the cost for these UTIs. As such, any payer 424 is likely the party most likely to prefer reduction of UTIs. Finally, examples of potential payers 424 could be insurance companies, Medicare, and other private payers.

Every measurement collected by the system is ingested by the high throughput data warehouse 314. Measurements are then analyzed by the risk factor identification engine 316 that uses coded as well as anomaly detection algorithms. Upon identification of risk factor(s), an alert chain is created and intervention delivery mechanisms are activated. An audit time stamped trail is set up to measure intervention performance and outcome impacts.

Figure 5:
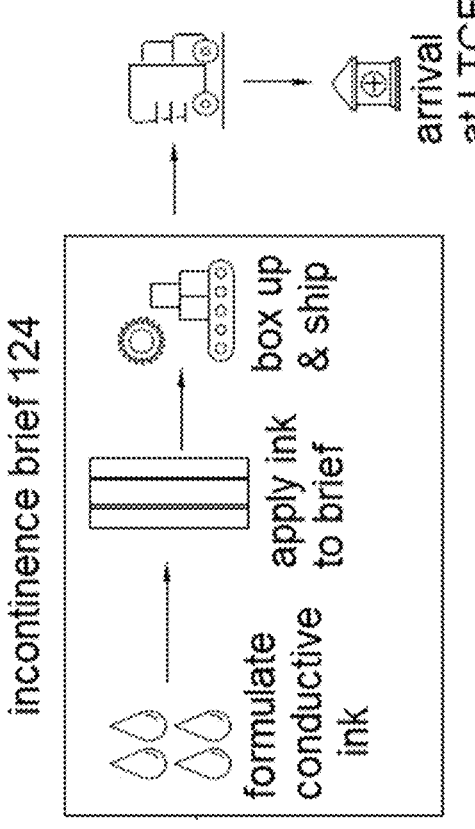
FIG. 5 shows detail about potential embodiments of a brief (garment)

FIG. 5 shows some more detail about potential embodiments of the brief (garment) 124. The ecosystem 100 utilizes the enhanced adult diaper brief 124 for accurate detection and collection of incontinence data. A standard adult diaper brief film backing is modified to include conductive ink strips such as disclosed within U.S. Pat. No. 10,561,541 Issued Sep. 11, 2018, the entire contents of which are hereby incorporated by reference. Such an implementation allows for diaper brief manufacturers to produce these enhanced diaper briefs without modifications to their existing manufacturing processes and equipment.

FIG. 5 shows a simplified view of a potential processing for making and shipping the incontinence brief 124. From FIG. 5 it is apparent that a conductive ink is formulated, and then applied to a specially-configured garment (brief) 124. These are boxed up and shipped according to specific customer orders. Exact requirements may vary from one LTCF to another.

Modified Call Light Module 136

Figure 6:
FIG. 6 shows an example modified call light module.

FIG. 6 shows an example modified call light module 136. In any LTCF, the call lights are one area in which responsiveness to patients can always be improved. While call lights are a well-known and even antiquated feature of LTCFs and SNFs, they are still ubiquitous in LTCFs, and yet can still be modernized to improve a patient's experience and overall effectiveness of the LTCF.

Accordingly, the modernized call light module 136 is a non-invasive method of monitoring a call light going on and off by means other than strictly visual. The principle of non-invasiveness is advantageous for being retro-compatible. An entire-new light fixture is not required, the call light module 136 can be adapted to existing call light equipment. The device will wirelessly send data to the data hub 112 to record "on" and "off" transitions.

One unique aspect of the call light module 136 is an ability to attach without any modification of the existing call light systems. Useful information can be obtained without a major re-work of the LTCF's electrical or lighting infrastructure. This is in keeping with the theme of the ecosystem 100 as a platform, in which a variety of equipment can used therein, both existing legacy equipment (e.g. call lights) as well as customized add-ons.

Accordingly, the modernized call light module 136, with the new bed elevation 140, and other new pieces, all act to better-inform the staff about patient needs.

The modified call light 136 contains a device that connects the ecosystem 100 to the older antiquated existing call light, including even the ancient dome light over the door. The modified call-light device 136 monitors when this light goes on, and off. It can be e.g. a circuit board 137 with a mechanical clip that clips onto the electric feed to that specific light, and senses when electricity is flowing and detects intensity of light, and indicates this status over e.g. Bluetooth, WiFi or other wireless means 138. This modified call light 136 can be rechargeable, solar, low voltage, with a low current drain.

Various LTCF staff have suggested that some diligent workers often don't notice the call lights, because the sound-component is not always working and\or the light is high above the door so they don't always see the visual indicator. Further, a hallway may have a window or skylight, such that during the day, sunlight floods that hallway. There also may be competing ambient light in a typical hallway or corridor, making the glow of a call light easier to overlook. The call light module 136 helps address these and other issues.

For example, assuming that a call light goes on, the call light module would notify the ecosystem 100 to summon e.g. a nurse aide or other level of health care professional. Lets them know the call light for e.g. room 382 is on. Of course the health care professional may have already seen the call light, but as explained above, there are instances where even a diligent professional may miss the call light. Using the call light module 136 and the ecosystem 100, that nurse aid knows she needs to get to that patient, and the ecosystem 100 monitors how long it takes her to arrive.

The call light module 136 thus helps provide better info about patient care data and worker responsiveness, and issues reports for management showing how long workers take to respond to call-ins. Specifically, the data hub 112 will send an intervention alert when a call light goes on, likely using the IDE 148.

Next, the ecosystem 100 also helps gather seemingly disparate data, such as a noticeable correlation between call lights and patient falls. Some portion of these falls are related to staff not answering call lights timely. Call lights can also be helpful to identify potential high risk fall patients. Some patients that do not get an answer to their call light, some patients will get up and try to walk.

Using an example of somebody that is continent, but not wearing the brief 124, now add they have a recently fractured hip. They are not supposed to ambulate on their own, but they are laying there in that bed and want to urinate. They're hitting that call light and yet nobody comes. Some patients may say "I refuse to lay here and pee on myself. I intend to get up and try to go to the bathroom on my own". Patients can fall as a result of that. Even without a fall, patient dis-satisfaction is evident. It is a goal of the embodiments herein to improve patient outcomes.

Running data through the centralized data hub 112, creating alerts, monitoring how long it takes people to get there, and managing staff's behavior and rewarding them for good behavior.

On the dehydration side, or even UTI detection, there are few Prior Art offerings that are reliable, and certainly not suitable for doing continuous monitoring. But, this field is improving and the embodiments herein stand ready to accommodate any improvements, acting as a platform 100 that can incorporate good ideas from $3^{rd}$ party developers as these become available.

Workflow and Example Method of Operation

The on-body 104 and off-body 108 sensors and other data sources collect real-time data related to at least patient health state, patient behavior, patient environment, and caregiver behavior. Data from various sensors and sources is delivered to the centralized data hub 112. The AI Engine 344 (FIG. 3) processes and analyzes the data to identify patterns, anomalies, and risk factors. The patient-specific health fingerprint 116 is thus established and maintained.

A non-limiting example flowchart of successful operation of the ecosystem 100 is shown in FIGS. 7A-7B below. The examples of UTI (FIG. 7A) and feeding tube (FIG. 7B) issues are shown because these issues are so expensive, and such a headache for LTCFs and for payers 424. However, these same principles apply to literally hundreds of other medical conditions found in LTCFs.

FIG. 7A shows a UTI example, in which the health fingerprint 116 is leveraged in order to target potential UTIs before they happen, or cut them off at a very early stage. Each UTI-related intervention, including both successful and non-successful (e.g. in which a patient must be moved to a hospital, or other expensive maneuver) are fed back to e.g. the central data hub 112 and other potential resources for additional learning and improvement or predictive factors. One beneficiary of the flows of FIGS. 7A and 7B is the payer 424 (see FIGS. 1, 4) who works with insurance companies, Medicare, and other reimbursement resources. All payers 424 are incentivized to reduce costs where possible, and the ecosystem 100 provides many ways to reduce costs without curtailing good patient care.

FIG. 7B shows a feeding tube example. Patients on feeding tubes are very impaired and typically require expensive types of care. Anything that can improve their quality of life and detect negative events as early as possible is a benefit. Its very easy to make a mistake with people on feeding tubes, conditions change quickly and can have enormous consequences.

Begin GUI Section

Within this disclosure, there will be many non-limiting GUI representations in the various Figures. These GUIs may appear in various formats within the web dashboard 172, digital signage 176, and aspects of the reporting services 208, including other locations as well.

This disclosure aims at a very wide audience, including persons with minimal computer-sophistication and others with much higher sophistication. Accordingly various Figures herein will show computer-user GUIs reciting one or more of intervention response times; improper device usage; types of interventions; aggregate counts of alerts; and other statistically significant data. In order to not clutter or over-complicate the Figures herein, the GUIs herein will be considered to be simplified, skeletal versions that may not be an exact replica of actual-use GUIs, but still convey the main and important features within the ecosystem 100 sufficient for a POSITA to build the embodiments.

The outcome based reports 416 are generated at statistically viable intervals e.g. daily weekly monthly or some other arbitrary period. These reports calculate financial impact based on a reduction of negative health outcomes which result in acute care. This feature is critical to insurers and HMOs. An ability to forecast and manage costs is a boon for insurers and the entire sub-industry of entities involved in financing LCTFs and SNFs.

FIG. 8 shows an example non-limiting GUI derived from either the wrist wearable device 120 or some other device which effectively measures body temperature, heart rate and blood oxygen levels one time per pre-agreed time period on each resident. The alert thresholds are individually set to alert (trigger) for each resident depending on baseline data, and nursing criteria, and the health fingerprint 116 that is unique for each patient.

The GUI of FIG. 8 illustrates how the ecosystem 100 contains various technology-elements and data-predictive elements especially well-suited for triggering appropriate (non false-alarm) nursing alerts for temperature and possible fever, abnormal heart rate and low blood oxygen levels. Just based on the simple easy-to-understand conditions of pulse, pulsOx, and body-temp, 288 (40+92+156) triggers of alerts occurred. Some of these were resolved by various means, but just based on these 3 simple parameters, 115 targeted interventions and bedside assessments by licensed nursing staff occurred, with 39 instances of physician-notified events.

Without the ecosystem 100, these intervention-numbers might have been much lower, which in turn means eventual discharges to ER or hospital might have been much higher.

In other words, the ecosystem 100 quickly detected 115 new nursing interventions and 39 physician interactions. However, only a single ER visit and one hospitalization was necessary. That is a good ratio.

An end-result is that the ecosystem 100 is effective in alerting on potential condition changes resulting in expeditious bedside assessments and treatment, where these treatments occur quickly, in-place, and avoid expensive and complex hospitalization and transport.

Another application of the ecosystem 100 is shown in FIG. 9, which shows a GUI displaying various improvements in incontinence care and skin health produced through utilization of the ecosystem\platform 100.

Within this disclosure, the expression "skin breakdowns" is roughly equal to bedsores, or perhaps "open wounds", having e.g. 4 stages as shown in FIG. 9. The ecosystem\platform 100 alerts staff immediately when an incontinent event occurs. The centralized data hub 112 tracks and reports the time it takes a staff member to respond and provide incontinence care. It can be seen from this data that in over 5,500 patient days of monitoring these residents the ecosystem 100 responded to over 31,000 incontinent events.

Prior to alerting staff and collecting response time data, some initial data was collected to establish a baseline for staff response from LTCFs not utilizing the ecosystem 100. The LTCFs not utilizing the ecosystem 100 demonstrated a baseline of 6.25 hours for staff to respond to provide care for an incontinent episode. This data further demonstrates that the ecosystem reduced the 6.25 hours of staff response time to an average of 1.44 hours.

FIG. 9 shows that within a given time period, a financial rewards system was implemented that provided monetary rewards for faster staff response times. After implementation of this rewards program, staff response time was reduced to 0.90 hours. Poor incontinence care and poor peritoneal care are directly linked to nursing home skin breakdown and Urinary Tract Infections (UTI's). All residents utilizing the technology were monitored for the development of skin breakdown and UTIs. It can be seen from FIG. 9 that the ecosystem 100 was highly effective in preventing both of these negative outcomes.

The GUI shown in FIG. 9 reinforces that the ecosystem\platform 100 is effective in improving incontinence care and reducing nursing home resident skin breakdowns. The GUI shown in FIG. 9 also reinforces that the ecosystem\platform 100 is effective in detecting, tracking, and early-intervening potential development of UTIs, thereby achieving improvements in incontinence care.

Next, FIG. 10 shows alerts managed by the ecosystem\platform 100 suitable for monitoring individual resident incontinent episodes for bowel and bladder. Collection of this data relates to the high incidence of hospitalizations from nursing homes with a diagnosis of dehydration and fecal impactions. To address these and other issues, the ecosystem\platform 100 is adjustable and can be configured for specific environments. The GUI of FIG. 10 shows a setting to alert licensed nursing staff if a resident does not urinate within a 6 hour period, thereby triggering staff to provide fluids to the resident. Similarly, the software is currently set to alert licensed nursing staff if a resident does not have a bowel movement within a 72 hour period. All kinds of other numbers and metrics are also settable and changeable, so that these specific numbers were used solely for non-limiting example.

From the GUI shown in FIG. 10 it is apparent that in 5642 patient days the system issued 108 decreased urinary output alerts and 54 fecal impaction alerts. While some of these may have been discoverable via conventional means, having this expanded data is helpful for problem solving and accuracy. The software further recorded a 100% accuracy in triggering bedside nursing assessments. Over 90% of these alerts resulted in new nursing interventions or physician orders. Meanwhile, there were no emergency room visits or hospitalizations for these alerts. This is very unusual. Contrasting FIG. 10 with normal standard statistics from a conventional LTCF, would show a big difference in expensive emergency room visits and hospitalizations.

From this and other Figures, it should be apparent that the ecosystem\platform 100 is highly effective in alerting staff to the potential for dehydration and fecal impactions and avoiding potential negative clinical outcomes.

Incentive Mechanisms and LTCF Worker Satisfaction

At this point it is now appropriate to discuss a novel approach to the worker $incentives 152 (FIG. 1). As stated, the various caregivers within an LTCF using the ecosystem/ platform 100 are rewarded for maintaining healthy behaviors that enable them to provide high quality of care. Rewards are based on adherence to quality metrics set by the ecosystem 100.

Figure 11A:
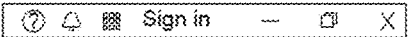
FIG. 11A shows substantial reductions in turnover of staff for an LTCF using the ecosystem compared to national and state averages using conventional LTCF systems.
Figure 12:
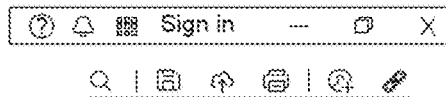
FIG. 12 shows an example "Reward Points" report in the format of a spreadsheet.

Some example incentive GUIs are shown in the FIGS. 11A, 11B, and 12. FIG. 11A shows substantial reductions in turnover of staff for an LTCF that uses the ecosystem 100 compared to national and state averages. As shown in FIG. 11A, the CNAs (Certified Nurses Aids) that use the technology of the ecosystem 100 and get the rewards points have close to zero turnover, 1%. This is significantly lower than state and national averages.

In FIG. 11A it is apparent that 55 CNAS are under measurement in a time period spanning February, March, and April. During this time there were 55 of the CNA staff that received retention dollars or rewards dollars and where only 1 of the 55 in that time period left the employment of that facility. Meanwhile, the national turnover rate is around 53% and Kansas is at 58%.

Some employees have said "I wouldn't want to work anywhere where I didn't have this technology (ecosystem 100)". Many LTCFs don't have any technology that they use to help them manage their day, and that makes a CNA tasks harder. Much of their energy and goodwill is dissipated in ways that are not 100% productive.

Meanwhile, the same CNA workers see the ecosystem 100 as an organizational tool to manage their day from an efficiency perspective, somewhat how the rest of us may use e-mail, Office, Outlook, or Excel to efficiently manage their day from an electronic perspective. It's like they have an assistant and an aid that tells them the best most optimal use of their time. They don't look at the ecosystem/platform 100 as a "big brother" Truman Show or "Rat in a Maze" mechanism. Indeed, quite the opposite.

For example, a nurse aide is supposed to make a round and change people every two hours, morning, noon, and night. This sometimes results in changing people who aren't soiled. At the same time, this wasted effort may prevent them from getting to someone who authentically needs help. This also leads to waking people up in the middle of the night, lifting them up with a Hoyer lift, and changing them unnecessarily.

Moving on to hospitalizations (e.g. FIG. 8), the most expensive part of the whole healthcare system is the acute care side. This refers to hospital stays and readmission rate from nursing homes to hospitals in the first 30 days, and it's 20 to 25% and they're also going back often. An example payer 424 is strongly incentivized to reduce such costs, sometimes unfortunately at the sacrifice of quality of patient care.

Multiple studies on admitting diagnosis on people admitted to the hospital from a nursing home. Touching on some of the high incident areas. In wounds it's easy. There's a lot of studies that calculate the cost of wound care. FIG. 9 shows the 4 stages of wound care.

UTIs lead to sepsis. Sepsis leads to ICU. Patients are either in the ICU or in a step down unit. All parties want to avoid these outcomes. Preventing skin wounds is close to as important as preventing UTIs, and skin wounds at least have a leading indicator that can be tracked, which is fever. The ecosystem 100 is excellent for picking up fevers quickly. The idea is to either prevent fevers or rapidly detect fevers and treat them in-place.

Next, in any hospital room its possible to see a patient hardwired to a lot of technology on the wall monitors, monitoring heart rate, maybe blood pressure, blood oxygen levels. However, note that there is no temperature indicator.

With all that technology, they still must visit a patient to do a temperature check, and must bring in a thermometer. It's either forehead or sublingual. Today, finally, the technology around temperature is improving. For example, a version of the watch wearable 120 has an infrared sensor in it for temperature. Not just using skin temp (sometimes inaccurate, and/or imperfect correlation with fever), but using infrared. This simple connection gives the ecosystem 100 an extra advantage to detect fevers, infections, and maybe (more indirectly) UTIs. Thus, something as simple as more effective temperature-taking, can produce profound results.

Another annoyance is continuously waking up and monitoring these patients for fever, putting something in their mouth, the old fashioned intrusive and not-fully-reliable way. Fevers are the first indication for a lot of things. Most fevers are infections, they're UTIs, potentially sepsis, pneumonia, COVID, whatever makes a body react with an immune response. Usually it's viral or bacterial. One could have a fever, but could lie in a nursing home for a long time with a fever before anybody noticed. And a patient may be unresponsive before it's detected.

A functional human will know if they are spiking a fever, and maybe if it's one of their kids. But lying in a nursing home that's understaffed, back at the end of the hallway in room 392, with a low grade fever of a hundred or 101, there's a really good chance no one will notice that person being in the throes of infection.

Thus, one value of the ecosystem 100 is its ability to not let fever go very long. Early intervention is immensely more helpful than getting to a patient even just a bit too late.

There are certain things that can go wrong in a LTCF or SNF, e.g. fevers. There are certain needs that are constantly happening throughout the day and they're just not being identified quickly enough, or they're being ignored or neglected. This is not a statement of worker apathy. Instead, these are difficult things to detect. Again, the ecosystem 100 has an ability to not let fever go very long without detection, and can keep a worker focused on the areas of most need, and not doing busy-work or unhelpful tasks.

Accordingly, the ecosystem 100 provides a concept of care and blanketing a nursing home with technology and leveraging that technology in such a way that it actually achieves process outcomes including changes in staff behavior, leading to reduced turnover (FIG. 11A).

FIG. 11B shows another wrinkle on top of FIG. 11A, and that is a type of evidence-based computation that is normally difficult to obtain. Specifically, the concept of prevention of hospital admissions, or situations where without a quick intervention, that situation would have assuredly ended up in hospital admissions. The ecosystem 100 provides an effective way to verifiably and objectively measure such preventions. In FIG. 11B, the state of Kansas was used as an example of a) somewhere in which no LTCF uses the ecosystem 100, and b) somewhere in which state-wide LTCF measurements are likely carefully tracked.

FIG. 11B shows how the ecosystem/platform 100 provides a high volume of data, multi-layered and having numerous complex interconnections. As such, it is anticipated that there will be a wide variety of potential customers for the data provided thereby.

Accordingly, the suggested data-format within the GUI of FIG. 11B is merely to show one example of data that is not typically provided by other LTCF systems. The example GUI shown in FIG. 11B may not even be the most in-demand GUI, but instead is just one example of providing helpful data that can be very difficult to tease out using conventional LTCF measurements. Meanwhile, within the ecosystem/platform 100, this data is quickly available. There are likely 100 other GUIs and data points that are also just as practical and helpful, but for brevity are not presented herein.

FIG. 12 shows an example "Reward Points" report in the format of a spreadsheet showing different alerts and their types, time to resolve, specific employee, and other details. The employees have an incentive to produce better outcomes, and have the means to do so since the ecosystem 100, the intervention delivery engine 148, and the worker mobile app 156 make it easier for a LTCF worker to "go find your money".

This ends the section on employee incentives. More information about a potential framework can be found in Appendix A, at the end of this disclosure.

Networking, Communication, Catch-all for Remaining Features

The various on-body (wearable) 104 and off-body (environment) 108 devices within the ecosystem 100 utilize multiple wireless RF communication mechanisms that include the following but are not limited to Bluetooth, Zigbee, Zwave, NFC, and/or WiFi. Fortunately, this variety of protocols is managed by the ecosystem 100 itself, so that the users and caregivers need not carry multiple devise and constantly be updating and adjusting communication parameters and app updates.

Further, the ecosystem/platform 100 accommodates the fact that in any nursing home, a plethora of mobile and IoT devices exist, belonging to either the patients, their visitors, or other persons.

Instead, the ecosystem/platform 100 does not compete with the general population for networking resources, WiFi, or cell-tower access. Instead, the ecosystem\platform 100 provides its own stand-alone resources and infrastructure so that all devices within the ecosystem\platform 100 do their communicating entirely therewithin. Thus, the ecosystem platform 100 has its own infrastructure and is thus entirely indifferent to whatever kinds of mobile breakdowns or outages or weak signals that may be harming the general population.

A secondary layer of dynamic encryption is used on all RF communication by devices, partly to satisfy HIPAA patient-privacy issues. Dynamic encryption is based on a device specific encryption key that is generated for each device by a global key vault mechanism. Device specific encryption keys are designed to be revoked and changed when security threats are identified.

A mesh technology is implemented on all devices on-body 104 or off-body 108 and is managed by the signal hub 112 directly connected to the network and is responsible for sending data to the cloud 312.

The intervention delivery engine 148 monitors staff performance, assigns points based on set performance metrics that are tied to intervention response times, converts points to a monetary equivalent, and conveys the monetary reward.

Alerts come in a wide variety include multiple levels or urgency, and comprise air quality, abnormal heart rate, abnormal behavior/patterns/movement, medication reminder, medication tracking, hydration level (dehydration), blood oxygen (Oxi Tracker), breathing alerts, senior care alerts, fall detection, cognitive function decline/change, quality of sleep (e.g. REM monitoring) and other alerts associated with current and future biomarkers as they are developed. All alerts are time stamped and connected to alert chains to record reminders, escalation levels and repeated alerts that are tied to the same risk factor.

As stated, the ecosystem 100 is also designed to be a platform, facilitating $3^{rd}$ party developers of new sensors, biomonitors, and health-data devices. Accordingly, the various sensing mechanisms overtly shown here are for example only and should not be considered limiting.

An alert-specific intervention process is generated for each patient. During intervention it is ensured that the caregiver is physically near the patient. This is accomplished by having the caregiver physically touch, view, and assess the patient at each intervention, where an assessment is recorded by the ecosystem 100.

The intervention delivery engine 148 responds to an identified risk factor by creating an alert and setting up an alert chain. Appropriate response time tracking is set up and the alert is sent to the caregiver via the mobile app 156.

The ecosystem 100 allows for creation of caregiver accounts for authorized access to mobile and web applications. The ecosystem 100 also allows for the entry of patient information into the system as well as management of patient specific parameters. This is all incorporated into the patient health fingerprint 116.

The ecosystem 100 monitors status of all devices 104\108 and issues alerts when device maintenance is required. Multi device chargers allow for efficient recharging of battery operated devices.

Using the mobile app 156, caregivers receive audible, visual and haptic notification of an alert with appropriate information to conduct an intervention. In an embodiment, these notifications are triggered by the Intervention Delivery Engine (IDE) 148. Alerts and interventions are communicated through a mobile device application that utilizes WiFi and cellular connection for communication with the ecosystem 100.

Early detection of health risk factors and anomalies are extremely important to best facilitate productive and well-targeted interventions that prevent negative health outcomes. Unfortunately, in many LTCFs, workers are motivated and doing their best, but often lack sufficient information to know what specific intervention to take.

To address this and other problems, behavior tracking includes monitoring and analysis of user behavior to detect abnormalities. These include but are not limited to mood, cognitive function, and physical activity. Meanwhile, environmental monitoring includes tracking various environmental variables that can lead to health risks and facilitating interventions. These include but are not limited air quality, humidity, temperature, noise levels, light Intensity, call lights 136, and proper bed elevation 140.

By integrating all these components, the ecosystem\platform 100 creates a comprehensive mechanism that improves health monitoring, risk detection, and personalized care delivery, along with providing a stable platform for future enhancement and innovations. As a result, negative health outcomes are reduced if not prevented, thereby improving quality of life and reducing frequency of acute care and/or hospitalizations.

Bed Elevation Monitor 140

The embodiments herein also accommodate retrofitting a conventional LTCF bed so as to better track specialized and high-risk patients such as tracheotomy patients, and ventilator patients. The head of their bed should be sitting at about 30 degrees because of the risk of that person aspirating fluids into their lungs if they lay flat. The ecosystem 100 keeps an eye on that bed elevation, the call lights, any incontinence, the data coming out of the watch 120, and other things.

Many Prior Art bed manufacturers have indicators of the angle of the bed just to inform the aid or the nurse what the angle is, but it doesn't look like anyone is actually monitoring it and then notifying the staff when the angle is incorrect for that person. Meanwhile, the embodiments herein tie back to the worker $incentives 152 where the employees and the facility engage in process-oriented quality measures. All of this (e.g. bed monitors) ties into the data for creating the incentives (rewards) 152, and it qualifies either the staff or the building for those rewards. Meanwhile, none of the Prior Art bed-resources are set up to let the staff know when the angle is wrong, thus they are all basically passive. They do not trigger interventions in the ways disclosed herein.

When caregivers arrive to provide care to the patients, they lower the head. Giving them a bed bath, incontinence care, sometimes they have to lower the beds to be effective. But when they leave, sometimes even a conscientious worker forgets to raise back up that head of that bed.

Using another feeding tube example, somebody's continuously being fed by a tube either directly into their stomach, a g-tube, or through the nose of the nasogastric tube. If they eat a full meal and go lay flat on-back for a while, all that food is all that liquid in their stomachs and they're laying flat on their back. There has to be a better way to avoid this problem, and fortunately the ecosystem 100 provides ways.

Next, many of these patients are physically deteriorated. So their odds of regurgitating that fluid up into the esophagus and then into the airway and the lungs is high. Gravity helps prevent that, but only if the workers take advantage of this gravity by remembering to raise-restore the head of the bed back to its appropriate position.

Same for somebody who's on a ventilator with a tracheotomy and they're coughing. Reflux isn't strong for anyone with a tracheotomy. These patients create mucus like crazy. All parties want such mucus to go to the stomach, not the lungs. Laying somebody flat creates a good chance of it going into the lungs. This leads to aspiration pneumonia. Fluids that aren't supposed to be in the lungs are reaching the lungs.

Tube feeding is especially risky. These are weak people. Imagine somebody with MS, or quadriplegic, or just generally debilitated and weak. If mucus-buildup happens to them, the odds of them being able to cough and clear and those kinds of things are minimal. So these are debilitated people in the first place. They may not have real strong cough or muscular ability to move fluids out of that airway. Accordingly, proper elevation ensures that gravity works in their favor as far as keeping fluids out of the lungs.

That's the point of the 30 degrees and that's the standard of care. Perhaps 30 to 45 degrees. 45 is difficult to do with some people, but a minimum of 30 degrees elevation is usually needed. Seeing a tube feeder laying flat on her back, that is usually unwanted. This is avoidable, regrettable, yet happens all the time. Even the most conscientious worker can use a reminder.

This applies to tracheotomy patients too, and ventilator patients. Attach a device to the head of that bed that will communicate whenever that thing goes below 30 degrees. Will alert (verb) when they're giving care. An embodiment could set up the bed to automatically raise back up the bed after an intervention, or alert a worker to raise it back up. An embodiment could set it maybe where it only alerts if it stays that way for longer than 10 minutes. There can be ways to "snooze" the bed for a bit, but then have it auto-attempt to restore back to 30 degrees.

The top 3 reasons that somebody's admitted to the hospital from a nursing home are UTI with sepsis, pneumonia, and then falls. There are many other conditions detected by the embodiments herein, so this is not meant to be a comprehensive list. But UTIs cost all of us a fortune.

Patient Dignity (Overcoming Helplessness)

The embodiments herein in some ways act as an extra person, an extra aid that helps them even though not a human. It's like an assistant alongside them. Various projects for paraplegics are occurring in East Texas, where otherwise such a person cannot make himself heard. The embodiments herein provide a voice for patients that can no longer talk. For those that have no way of communicating, the ecosystem 100 can be their mode of communicating that they need to be changed or need an aide. The embodiments herein become their only voice.

Next, consider a case in which somebody transitions from a LTCF to their home. As shown in FIG. 1, the ecosystem 100 offers the family app 160, the worker (caregiver) app 156.

Sensing Patient Mood

The ecosystem\platform captures data points from different devices, and has ways to figure out to look at initial expressions. Using e.g. a combination of looking at heart grade, looking at some mood issues. So in combination, the ecosystem 100 can detect some mood issues, e.g. poor sleep, inadequate REM, can affect mood.

Dehydration

Dehydration technology is still not performing well, but 2025 and 2026 are likely to be much better. In such a case, the ecosystem 100 would be helpful. If they're not wet and yet there has been minimal urine output, one can induce dehydration. The health fingerprint 116 can help compute this even in the absence of concrete data-points.

But dehydration equipment is coming, expected, that does not require in-mouth usage, does not require cheek-swabs, and yields more concrete data-points. The ecosystem/platform 100 stands ready to accommodate this when it becomes available.

That's why the ecosystem 100 is important as a platform for the future. That's why the 3rd party references are encouraged herein, because the idea of the platform is a great advantage. Any third party can come into a nursing home. They could technically set up their own Bluetooth, and do some of their own things. But then, they must give their nurse another device to carry? Have a nurse carrying this, and a nurse carrying that, and then another? No. Too many gadgets. Too many problems, CNAs can't work this way.

So a facility contemplating using the ecosystem 100 can note "oh good, our nurses need only carry one thing, just the front end to the ecosystem 100". Connect to the ecosystem 100, that will accommodate any 3rd party product. The ecosystem 100 is like a message "hey, just flow your data into the ecosystem 100, we will take it from there".

APPENDIX A: WORKER INCENTIVE STRUCTURE

What follows is an example non-limiting incentive structure for workers within the ecosystem/platform 100. All dollar amounts, time-limits, and other numerics below are adjustable and provided merely for example purposes. That is, these rules are dynamic and can be changed for each facility. The ecosystem 100 is designed to be able to dynamically change these metrics as needs change.

Quality Incentive Payment Program

Smart Brief Wearable Device: $45 per qualified patient day

Wrist Wearable Device: $25 per qualified patient day

Payment Incentive Qualification Requirements

The ecosystem 100 will monitor and qualify the patient day in 24 hour periods (12 AM to 12 AM) and apply payment criteria qualification and disqualification as follows:

Brief Wearable Alerts Penalty Threshold

Moisture Alerts (Urine/BM): All response times<=2 hours, where every response time>2 hours==a $5 reduction;

Decreased Urinary Output: All response time<=2 hours, where every response time>2 hours==a $5 reduction;

Decreased Fecal Output: All response times<=2 hours where every response time>2 hours==a $5 reduction;

Temperature Alert: All response times<=2 hours where every response time>2 hours==a $5 reduction;

Detachment Alert: All response times<=2 hours where every response time>2 hours==a $5 reduction;

Responding to any device alert more than 4 hours after it's issued will lead to a complete forfeiture of that day's payment eligibility.

Wrist Wearable Alerts Penalty Threshold

Temperature Alerts: All response times<=2 hours, where every response time>2 hours is a $5 reduction;

Pulse Alerts: All response time<=1 hours, where every response time>1 hour is a $5 reduction;

Pulse OX: All response times<=1 hours, where every response time>1 hour is a $5 reduction.

Payment Disqualification

Eligibility for full rewards is forfeited if the wrist device logs fewer than 10 measurements in a day due to improper placement or insufficient battery power.

Responding to any device alert more than 4 hours after issuance will lead to a complete forfeiture of that day's payment eligibility.

FIG. 12 shows an example GUI showing how various responders were economically rewarded for quickly responding to the most important LTCF tasks.

DISCLAIMER

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations, or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

What is claimed is:

1. A method of identifying and rectifying risk factors within a long-term care facility (LTCF), comprising:

locating and configuring a plurality of off-body and on-body sensing devices within a customized platform/ecosystem;

continuously polling the devices and combining health data from the devices to form at least one patient-specific health fingerprint for each of the one or more patients within the LTCF;

continuously collecting the health data according to a variety of individualized predetermined criteria inquiring as to whether a medically significant change to any of the one or more patients health fingerprints has occurred;

the step of continuously collecting the health data further comprising weighting some data higher and other data lower depending on the individualized predetermined criteria;

directing a garment specifically toward detecting conditions which are known to lead to a Urinary Tract Infection (UTI); and a UTI-danger event being a garment-indicated lack of urination for a predetermined amount of time; and in the instance where the patient is on a feeding tube, or has an IV drip containing nutrition, when such a UTI-danger event occurs, automatically increasing fluid intake without requiring any human intervention in doing so;

providing Graphical User Interface (GUIs) of hospitalization metrics including independent objective LTCF-to-hospital transition data across an entire industry and storing that data as LTCF-H1;

measuring the LTCFs using the ecosystem platform herein for their own LTCF-to-hospital transition data and storing that data as LTCF-H2;

comparing LTCF-H1 with LTCF-H2; and obtaining and displaying objectively quantifiable tangible decreases in hospitalizations that are proximately caused by the ecosystem platform and only the ecosystem platform.

2. The method of claim 1, further comprising:

the on-body sensing devices comprising a skin temp monitor, a body temp monitor, a glucose monitor, a heart rate monitor, a pulseOx, and an ECG monitor.

3. The method of claim 2, the on-body sensing devices further comprising a hydration monitor, a blood pressure meter, a cognitive function monitor, a UV exposure monitor, or wound healing monitor (smart bandage).

4. The method of claim 3, further comprising:

the off-body (environment) sensing devices comprising a call light monitor, a bed elevation monitor; and a room temperature monitor.

5. The method of claim 4, the off-body sensing devices further comprising a humidity monitor, an ambientNoise monitor, an air quality monitor, and a light intensity monitor.

6. The method of claim 5, further comprising:

the various on-body and off-body sensing devices combining their data to continuously create and update a plurality of health fingerprints each unique to a single specific patient;

a centralized data hub continuously refining and maintaining accuracy and currency of the plurality of health fingerprints; and doing so without requiring any human intervention.

7. The method of claim 1, further comprising:

the centralized data hub working with a signal hub to manage and coordinate the plurality of data signals originating from the on-body and off-body data sensors.

8. The method of claim 7, further comprising:

the signal hub managing all data signals but not digesting any data or making any health-based decisions;

the signal hub sending data to the data hub which makes decisions and communicate with an intervention delivery engine; such that the intervention delivery engine concentrating and packaging all interventions and all tasks to only a single mobile device bearing a worker app.

9. The method of claim 8, further comprising:

pre-screening intervention data to be targeted, accurate, and filtered to reduce false alarms;

the centralized data hub and intervention delivery engine screening, filtering, assign priority, and sorting among the high volume of medical data according to continually evolving criteria which varies over time and varies per patient;

thereby assuring that the information about the patient is targeted and accurate.

10. The method of claim 1, further comprising:

a clinical research data module collecting clinical data including allowing 3rd parties to use data for research, and allowing 3rd parties to put a device into the ecosystem platform for collecting clinical data for research.

11. The method of claim 1, further comprising:

arranging\configuring each patient-specific health fingerprint to comprise pulseOx, body temperature, breathing rate, medication index, pain levels, and incidences of lost consciousness.

12. The method of claim 11, the patient-specific health fingerprint further comprising a tension level, a presence/absence of feeding tube, and a patient-fall history.

13. The method of claim 1, further comprising:

further directing the on and off-body devices toward detecting aspiration of gastric juices (AGJ);

an AGJ detection event comprising a patient choking alert;

when an AGJ detection event occurs, mechanically adjusting an upper-body angle of a patient's bed to be at least 30 degrees from horizontal.

14. The method of claim 1, further comprising:

aggregating UTI data by state;

aggregating UTI data by insurance-region;

obtaining and affirming objectively quantifiable tangible proximately-caused UTI decreases in that same state; and/or obtaining and affirming objectively quantifiable tangible proximately-caused UTI decreases in that same insurance-region.

15. The method of claim 1, further comprising:

providing outcome reports showing what impact the ecosystem\platform had on patients including but not limited to reductions of UTIs.

* * * * *